United States Patent
Buchanan et al.

(10) Patent No.: US 9,613,185 B2
(45) Date of Patent: *Apr. 4, 2017

(54) INFLUENCE FILTERING IN GRAPHICAL MODELS

(71) Applicant: International Business Machines Corporation, Armonk, NY (US)

(72) Inventors: David W. Buchanan, Pleasantville, NY (US); Jennifer Chu-Carroll, Dobbs Ferry, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 230 days.

This patent is subject to a terminal disclaimer.

(21) Appl. No.: 14/463,787

(22) Filed: Aug. 20, 2014

(65) Prior Publication Data

US 2016/0055423 A1 Feb. 25, 2016

(51) Int. Cl.
  *G06F 19/00* (2011.01)
  *G06N 7/00* (2006.01)
  *G06N 99/00* (2010.01)

(52) U.S. Cl.
  CPC ......... *G06F 19/3437* (2013.01); *G06N 7/005* (2013.01); *G06N 99/005* (2013.01)

(58) Field of Classification Search
  None
  See application file for complete search history.

(56) References Cited

U.S. PATENT DOCUMENTS

| | | |
|---|---|---|
| 6,807,537 B1 | 10/2004 | Thiesson et al. |
| 7,430,475 B2 | 9/2008 | Imoto et al. |
| 7,720,779 B1 | 5/2010 | Perry et al. |
| 7,730,072 B2 | 6/2010 | Richter et al. |

(Continued)

FOREIGN PATENT DOCUMENTS

EP 2110779 A1 10/2009

OTHER PUBLICATIONS

Darwichem "Bayesian Networks—What are Bayesian networks and why are their applications growing across all fields?," Communications of the ACM, Review Articles, Dec. 2010, pp. 80-90, vol. 53, No. 12.

(Continued)

*Primary Examiner* — Alan Chen
(74) *Attorney, Agent, or Firm* — Cantor Colburn LLP; William Stock (57) ABSTRACT

According to an aspect, influence filtering in a graphical model includes accessing the graphical model in a data store. The graphical model includes a plurality of nodes connected by edges having edge strengths representing a degree of relation between the nodes. A target relation strength for a pair of nodes in the graphical model is received. An edge strength of an edge in a direct path between the pair of nodes is determined by traversing, in the graphical model, one or more paths other than the direct path between the pair of nodes. The determining also includes estimating a cumulative strength of the traversed paths, and calculating the edge strength for the edge in the direct path based on the cumulative strength of the traversed paths and the target relation strength. The calculated edge strength is assigned to the edge in the direct path between the two nodes.

9 Claims, 11 Drawing Sheets

(56) References Cited

U.S. PATENT DOCUMENTS

| | | | |
|---|---|---|---|
| 8,140,569 | B2 | 3/2012 | Hulten et al. |
| 8,554,618 | B1 | 10/2013 | Gasch |
| 2007/0094219 | A1 | 4/2007 | Kipersztok |
| 2010/0306166 | A1 | 12/2010 | Pantel et al. |
| 2012/0158636 | A1 | 6/2012 | Bowers et al. |
| 2012/0233100 | A1 | 9/2012 | Camerer et al. |
| 2014/0108322 | A1 | 4/2014 | Buchanan et al. |
| 2014/0250047 | A1* | 9/2014 | Bounouane ......... G06F 17/2765 706/52 |
| 2014/0337306 | A1* | 11/2014 | Gramatica ........ G06F 17/30731 707/706 |
| 2015/0149484 | A1* | 5/2015 | Kelley .............. G06F 17/30398 707/748 |

OTHER PUBLICATIONS

Yuille, et al., "The Noisy-Logical Distribution and its Application to Casual Inference," Dept. of Statistics, UCLA, Oct. 25, 2011, Cover page, pp. 1-8.

Charniak, Eugene, "Bayesian Networks Without Tears", AI Magazine, vol. 12, No. 4 (1991), pp. 50-63.

Mei, et al., "Robust RegBayes: Selectively Incorporating First-Order Logic Domain Knowledge into Bayesian Models", Proc. 31st Int. Conf. on Machine Learning, Beijing, China, Jun. 21, 2014 to Jun. 26, 2014, to be published in JMLR: W&CP, vol. 32 (in press at this time: Jun. 2014), 9 pages.

Agosta, John, "Approximating the Noisy-OR Model by Naïve Bayes", AAAI Technical Report SS-98-03, 1998, 6 pages.

Raghavan, Sindhu, "Extending Bayesian Logic Programs for Plan Recognition and Machine Reading", Doctoral Dissertation Proposal, 2011, 36 pages.

Golovin et al., "Near-Optimal Bayesian Active Learning with Noisy Observations", published Oct. 15, 2010, 9 pages.

Rosen et al., "Reasoning with BKBs—algorithms and complexity", Annals of Mathematics and Artificial Intelligence, vol. 40, No. 3-4, 2004, pp. 403-425.

List of IBM Patents or Patent Applications Treated as Related; (Appendix P), Filed Aug. 20, 2014, 2 pages.

David W. Buchanan, Pending U.S. Appl. No. 14/463,774 entitled "Reasoning Over Cyclical Directed Graphical Models," filed with the U.S. Patent and Trademark Office on Aug. 20, 2014.

List of IBM Patents or Patent Applictions Treated as Related; (Appendix P), Filed Aug. 16, 2016, 2 pages.

David W. Buchanan, Pending U.S. Appl. No. 14/644,340 entitled "Reasoning Over Cyclical Directed Graphical Models" Filed with the U.S. Patent and Trademark Office on Mar. 11, 2015.

David W. Buchanan, Pending U.S. Appl. No. 14/644,352 entitled "Influence Filtering in Graphical Viodels" Filed with the U.S. Patent and Tradmark Office on Mar. 11, 2015.

\* cited by examiner

INFLUENCE FILTERING IN GRAPHICAL MODELS

BACKGROUND

The present disclosure relates generally to graphical models, and more specifically, to influence filtering in graphical models.

Graphical models are widely used in artificial intelligence and machine learning. They are often used to represent the patterns of dependence between variables and to predict the distribution of some variables given some other variables. Much of the literature on graphical models has focused largely on learning graphical models from statistical resources. These might include correlations or conditional dependencies between variables. Another type of graphical model is one that is constructed based on one or more knowledge sources. For example, a phrase in a medical textbook such as "pneumonia causes fever in most patients" may be extracted and used to generate the knowledge that fever is present more often in patients that also have pneumonia, as compared to patients that do not have pneumonia. Post processing, such as relation extraction from natural language processing and/or querying a database of relations, may be performed on the extracted phrase to generate one or more relations associated with the phrase. The output of the post processing is a relational resource includes a set of relations that are then used to build a graphical model. When constructing graphical models from a relational resource, some issues arise that do not arise when constructing graphical models from a statistical resource. In particular, sets of relations from the knowledge source may be redundant with each other, causing an overestimation of the influence of one variable on another. Redundant sets of relations do not occur when graphical models are generated directly from statistical data, as influence can be estimated directly.

SUMMARY

Embodiments include a system and computer program product for influence filtering in graphical models. A graphical model in a data store is accessed. The graphical model includes a plurality of nodes connected by edges having edge strengths representing a degree of relation between the nodes. A target relation strength for a pair of nodes in the graphical model is received. An edge strength of an edge in a direct path between the pair of nodes is determined by traversing, in the graphical model, one or more paths other than the direct path between the pair of nodes. The determining also includes estimating a cumulative strength of the traversed paths, and calculating the edge strength for the edge in the direct path based on the cumulative strength of the traversed paths and the target relation strength. The calculated edge strength is assigned to the edge in the direct path between the two nodes.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Embodiments described herein relate to influence filtering in graphical models that are built based on information extracted from knowledge sources using a knowledge based method. As used herein, the term "knowledge based method" refers to building a graphical model from a relational resource that includes a set of relations between items. The set of relations can be sourced in a variety of manners such as, but not limited to: data mining; unstructured relation extraction; and knowledge base extraction. A resulting graphical model includes nodes representing items (or concepts), and edges representing the probabilistic dependencies (or confidence) between the items. Knowledge based methods can produce relations that are redundant with each other. For instance, A causes B, B causes C, and A causes C. This creates two redundant paths from A to C. Embodiments of influence filtering as described herein can be used to build graphical models from relational resources with redundant paths, and to adjust a strength associated with an edge between two nodes based on the strength of edges in other paths between the two nodes. Accounting for the strength of all paths between two nodes when assigning a strength value to a direct path between the two nodes provides a more accurate representation of the strength of the relation between the two nodes. As used herein, the term "direct path between two nodes" refers to a path that includes one edge that connects the two nodes.

Figure 1:
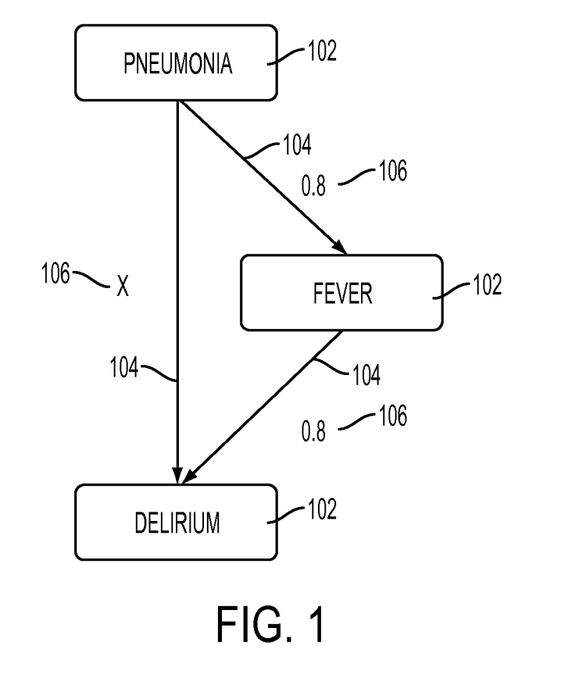
FIG. 1 depicts a block diagram of a portion of a graphical model in accordance with an embodiment.

Turning now to FIG. 1, a block diagram of a portion of a graphical model is generally shown in accordance with an embodiment. The graphical model includes several nodes 102, edges 104 (representing in this example, a "causes" relation) and edge strengths 106.

In the example shown in FIG. 1, the graph reflects that pneumonia causes fever with strength 0.8, and also that fever in turn causes delirium with strength 0.8. These two relations together imply that there is a relation between pneumonia and delirium, and in many contemporary graph semantics this would be interpreted as pneumonia causes delirium with strength 0.64 (i.e., 0.8*0.8). Suppose that relations are extracted from a knowledge source resulting in a list of three distinct relations: pneumonia causes fever with strength 0.8; fever causes delirium with strength 0.8; and pneumonia causes delirium with strength 0.64. In an embodiment the strengths are derived based on a knowledge base and/or assigned by a human annotator.

One approach to constructing a graphical model from these relations is to directly instantiate all three relations as edges in a graphical model. This is referred to herein as the "naïve approach" where each relation is directly added to the graphical model, and would result in the value "x" shown in FIG. 1 being assigned the value "0.64." In order to determine the strength of the relation between pneumonia and delirium, the graph would be traversed as follows: the strength of the edge between pneumonia and delirium (0.64) added to the combined strength of the edges between pneumonia and fever, and fever and delirium (0.8*0.8). The overlap between the two paths is then subtracted (0.64*0.8*0.8). The result of traversing the graph to determine the likelihood of pneumonia causing delirium using the naïve approach results in:

$$0.64+(0.8*0.8)-0.64*(0.8*0.8)=0.874$$

Thus, when using the naïve approach, the influence of pneumonia on delirium will be over-estimated even if list of relations extracted from the knowledge base is completely correct. This is because the graphical model treats the redundant edges as independent probabilistic evidence, but they are not.

Referring to FIG. 1, an embodiment uses an influence filtering approach to create a graphical model that can be used to correctly estimate the influence of pneumonia on delirium. As shown in FIG. 1, the strength 106 of the edge 104 between the nodes 102 labeled pneumonia and delirium is assigned the placeholder "X" and the graphical model is traversed as shown above and solved for X given that the known strength of the relation between pneumonia and delirium is 0.64:

$$X+(0.8*0.8)-X*(0.8*0.8)=0.64$$

$$X=0$$

Thus, the influence of pneumonia on delirium as reflected in the graphical model is already 0.64 and no additional strength needs to be added to the edge 104 between pneumonia and delirium. This implies that the edge 104 between pneumonia and delirium is redundant and embodiments of influence filtering remove this redundancy by assigning a strength of zero to the edge 104 between the pneumonia and delirium nodes 102.

As described above, influence filtering treats the relation "pneumonia causes delirium" as a statement about the total influence that pneumonia should have on delirium. If pneumonia already influences delirium in the existing graph, then this influence is considered and the corresponding edge in the graph that directly connects pneumonia to delirium is adjusted. In the example above, the existing influence of pneumonia on delirium is measured according to the semantics of the graph and the edge strength of the edge from pneumonia to delirium is set to be the edge strength needed to make the total influence the same as the strength of the relation in the received list of relations (e.g., in this example, 0.64).

In another example (not shown in FIG. 1), a knowledge source returns a list of three distinct relations: pneumonia causes fever with strength 0.5; fever causes delirium with strength 0.5; and pneumonia causes delirium with strength 0.8. The result of traversing the graph to determine the likelihood that pneumonia causes delirium using the naïve approach results in:

$$0.8+(0.5*0.5)-0.8*(0.5*0.5)=0.85$$

which overestimates the influence of pneumonia on delirium.

Applying an embodiment of the influence filtering approach described herein results in:

$$X+(0.5*0.5)-X*(0.5*0.5)=0.8$$

$$X=0.73$$

In this example, X (the strength of the edge 104 between the pneumonia and delirium nodes 102) is assigned the value of approximately 0.73 which results in the correct strength of 0.8 being calculated for the relation between pneumonia and delirium when the graphical model is traversed.

For purposes of illustration, noisy-logical Bayesian networks are used as a reference implementation and in the examples described herein. However embodiments are not constrained to such Bayesian networks and are applicable to other kinds of networks such as, but not limited to, Markov random field networks.

Also for purposes of illustration, the relation "causes" is used in the examples described herein. Embodiments described herein are not constrained to particular relations and may be used with any relation described by a graphical model.

Figure 2A:
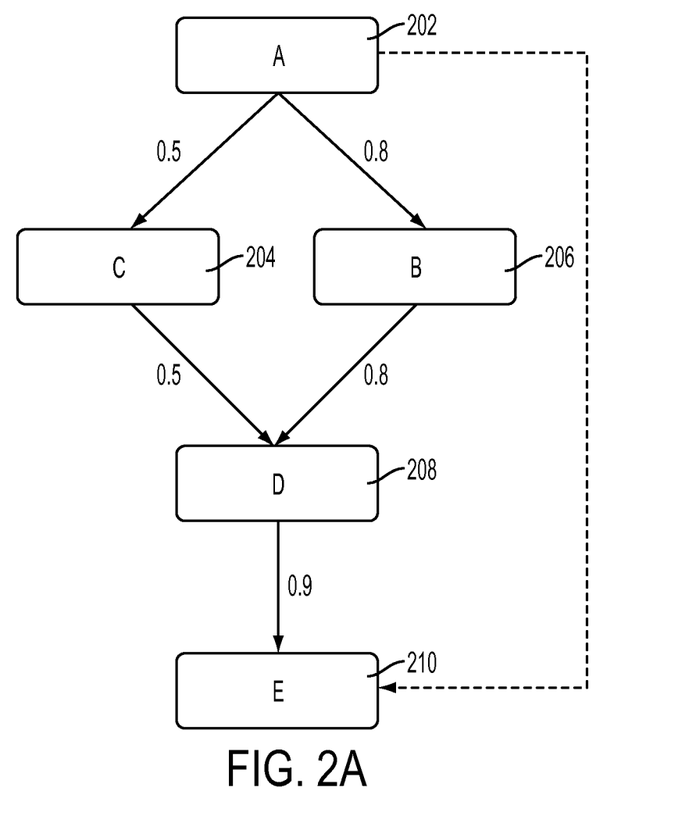
FIGS. 2A and 2B depict an example of implementing influence filtering in a graphical model in accordance with an embodiment.
Figure 2B:
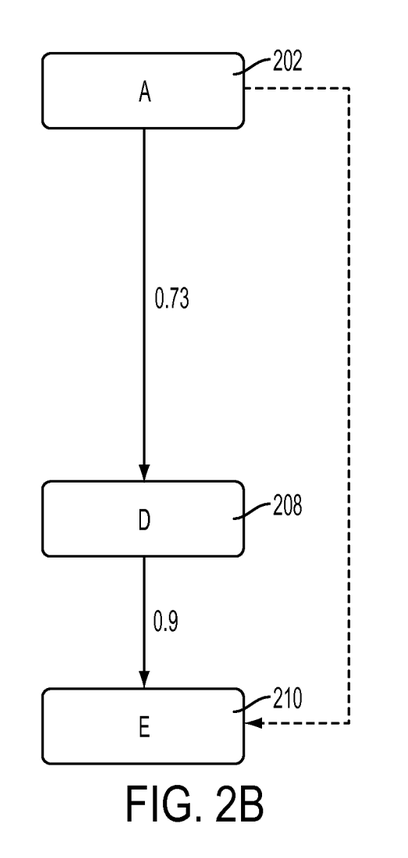

Referring now to FIGS. 2A and 2B an example of influence filtering for a path in a graphical model is generally shown in accordance with an embodiment. As shown in FIGS. 2A and 2B, the edge being filtered is the edge between node A 202 and node E 210 (AE). Before assigning a strength to the direct path AE, an estimate is made of the influence provided by all other edges, or paths, between node A 202 and node E 210. As shown in graphical model in FIG. 2A, there are two non-overlapping (parallel) paths between node A 202 and node D 208: node A 202 to node C 204 to node D 208 (ACD); and node A 202 to node B 206 to node D 208 (ABD). In an embodiment, the strengths of these parallel paths (ACD and ABD) are calculated and collapsed into a single path from node A 202 to node D 208 as shown in FIG. 2B. The strength of ACD can be calculated as:

$$0.5*0.5=0.25$$

and the strength of ABD can be calculated as:

$$0.8*0.8=0.64.$$

These strengths can be combined, for example, with a noisy-OR operation as follows:

$$0.25+0.64-0.64*0.25=0.73.$$

This result can be multiplied by the strength of the edge between node D 203 and node E 210 (DE) to determine the total existing strength of the path between node A 202 and node E 210 as follows:

$$0.9*0.73=0.657.$$

The strength of the relation between node A 202 and node E 210 prior to any strength being assigned to the edge that directly connects node A 202 to node E 210 (AE) is 0.657. If the total strength of the relation from node A 202 to node E 210 should be greater than 0.657, then a strength greater than zero is assigned to direct path AE. If the total strength of the relation from node A 202 to node E 210 should be equal to or less than 0.657, then a strength of zero is assigned to direct path AE.

For ease of description, the example shown in FIGS. 2A and 2B includes three nodes (node B 206, node C 204, and node D 208) and two sub-paths (ACDE and ABDE) between head (or parent) node A 202 and tail (or child) node E 210.

In an actual implementation, there can be hundreds or thousands or even tens of thousands of nodes and sub-paths between two nodes.

Figure 3:
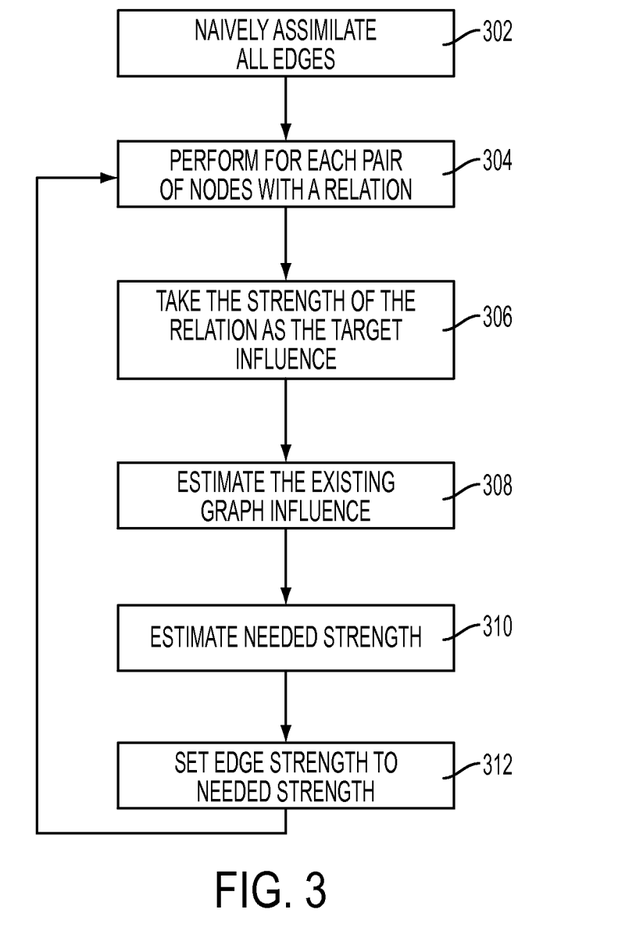
FIG. 3 depicts a process flow for influence filtering in a graphical model in accordance with an embodiment.

FIG. 3 depicts a process flow for influence filtering in a graphical model such as that shown in FIGS. 2A and 2B in accordance with an embodiment. At block 302, a graphical model is built from a list of relations (received from a knowledge source) using the naïve approach described previously where each relation between items is added to the graphical model as an edge between two nodes along with a corresponding edge strength. Next, block 304 is performed to initiate the processing in blocks 306-312 for each pair of nodes within a relation (e.g., node A 202 and node E 210 in FIG. 2A). At block 306 the strength of the relation between the two items (e.g., as indicated in the list) is assigned as the target influence between the nodes.

Processing continues at block 308 where the existing influence on the strength of a relation between the nodes is estimated by examining strengths of the edges of paths connecting the two nodes using a method such as that described above in reference to FIGS. 1, 2A, and 2B. The existing influence is also referred to herein as "the cumulative strength."

In an embodiment, the existing influence is estimated at block 308 by running probabilistic inference with the edge that directly connects the two nodes absent. The influence of A on B can be obtained by measuring the difference between B's inferred value when A is on, compared to when A is off.

In an embodiment, a heuristic algorithm is used at block 308 to estimate the existing influence by identifying paths of length "k" or less from head to tail. The paths can then be combined, as shown in FIG. 2B using graph semantics (e.g., a noisy-OR operation). Any loss of data caused by selecting a subset of the paths (e.g. the shortest paths) may be minimal because longer paths between nodes carry less influence.

At block 310, the needed strength can be estimated by subtracting the existing influence from the target influence. The edge strength of the edge that creates a direct path between the nodes is set to the needed strength at block 312. The process that includes blocks 306-312 is repeated for each pair of nodes in the graphical model that correspond to a relation specified in the list of relations received from the knowledge source.

Figure 4A:
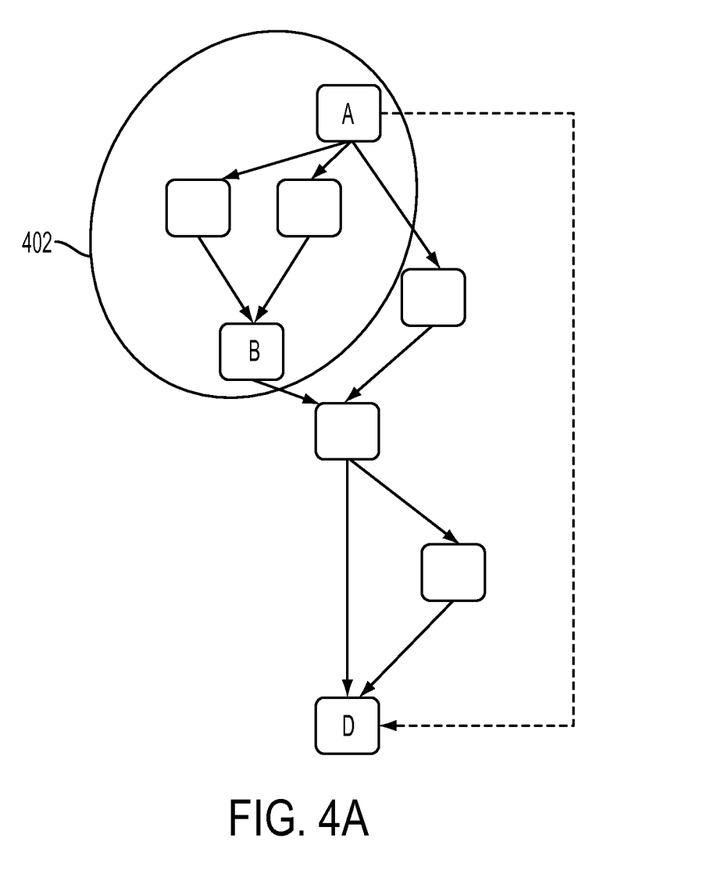
FIGS. 4A, 4B, 4C, 4D, and 4E depict a generalized recursive approach to influence filtering in accordance with an embodiment.

FIGS. 4A, 4B, 4C, 4D, and 4E depict a generalized recursive approach to the heuristic algorithm described above in accordance with an embodiment. The graphical model shown in FIG. 4A represents nodes and edges between nodes, where each edge represents a relation between a pair of nodes and includes a strength. As shown in FIG. 4A the node labeled "A" and the node labeled "D" have a relation (e.g., "A" cures "D" or "A" is a "D"). Embodiments described herein utilize influence filtering to determine a strength value to assign to an edge between the node labeled "A" and the node labeled "D." As shown in FIGS. 4A-4E this can be performed using a recursive process.

Figure 4B:
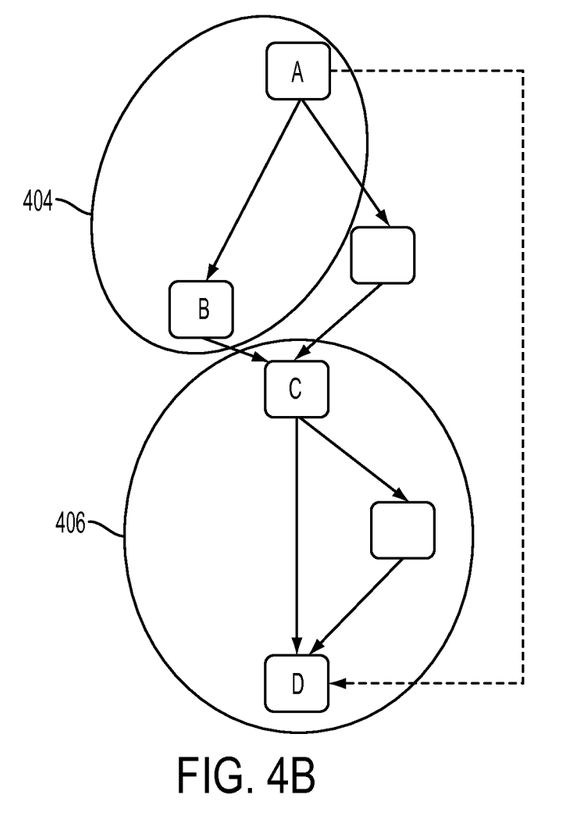

FIG. 4A shows a portion 402 of the graphical model that includes two parallel paths between the node labeled "A" and the node labeled "B". As shown in FIG. 4B, the strength of the two parallel paths is combined into a combined strength (or influence) value and reflected as a single (direct) path 404 between the node labeled "A" and the node labeled "B".

Figure 4C:
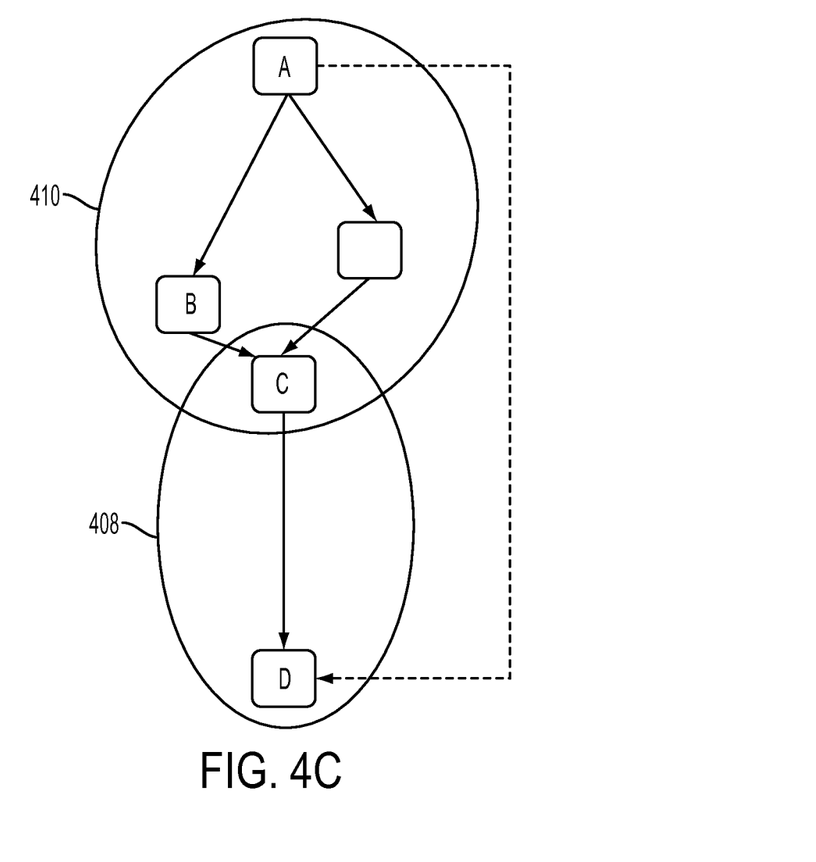

FIG. 4B shows a portion 406 of the graphical model that includes two parallel paths between the node labeled "C" and the node labeled "D". As shown in FIG. 4C, the strength of the two parallel paths is combined into a combined strength (or influence) value and reflected as a single (direct) path 408 between the node labeled "C" and the node labeled "D".

Figure 4D:
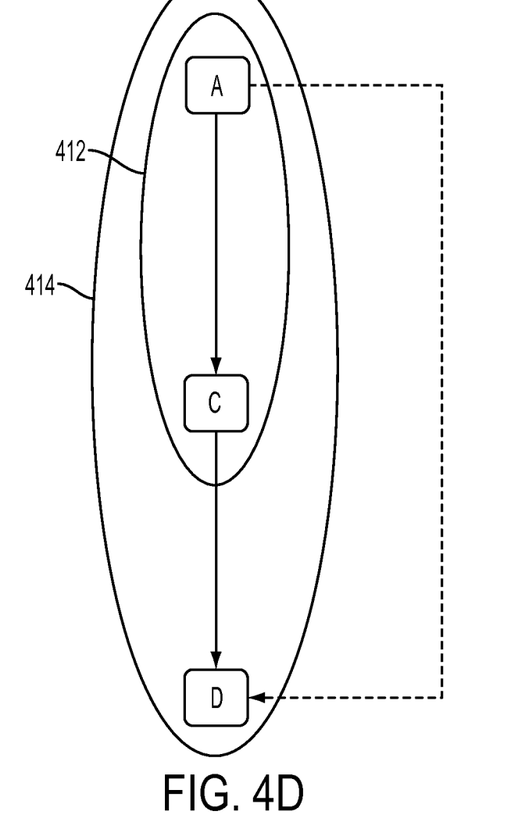

FIG. 4C shows a portion 410 of the graphical model that includes two parallel paths between the node labeled "A" and the node labeled "C". As shown in FIG. 4D, the strength of the two parallel paths is combined into a combined strength (or influence) value and reflected as a single (direct) path 412 between the node labeled "A" and the node labeled "C".

Figure 4E:
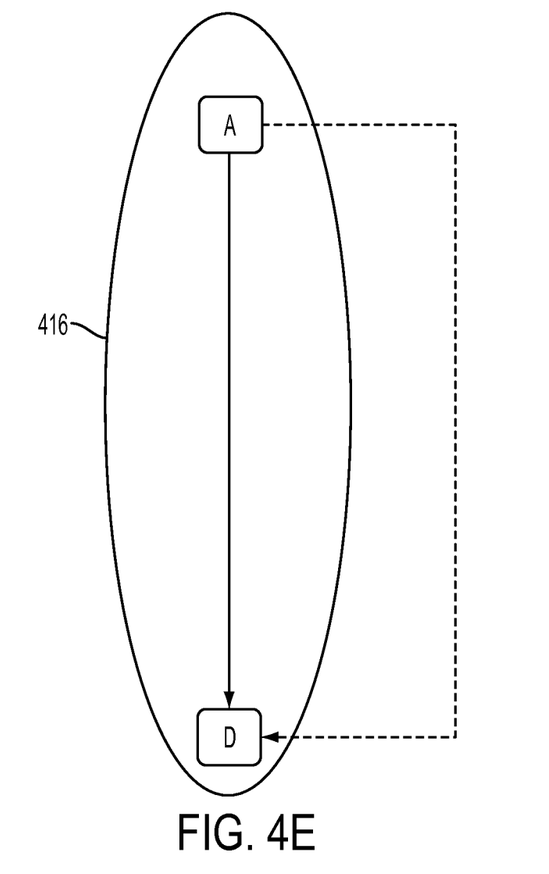

FIG. 4D shows a portion 414 of the graphical model that includes two sequential, or overlapping, paths between the node labeled "A" and the node labeled "D". As shown in FIG. 4E, the strength of the two sequential paths is combined into a combined strength (or influence) value and reflected as a single path 416 between the node labeled "A" and the node labeled "D". In this manner, the estimate of the existing graph influence can be calculated using influence filtering. Based on the results and a target strength, a strength value can be assigned to the edge between the node labeled "A" and the node labeled "D."

Figure 5:
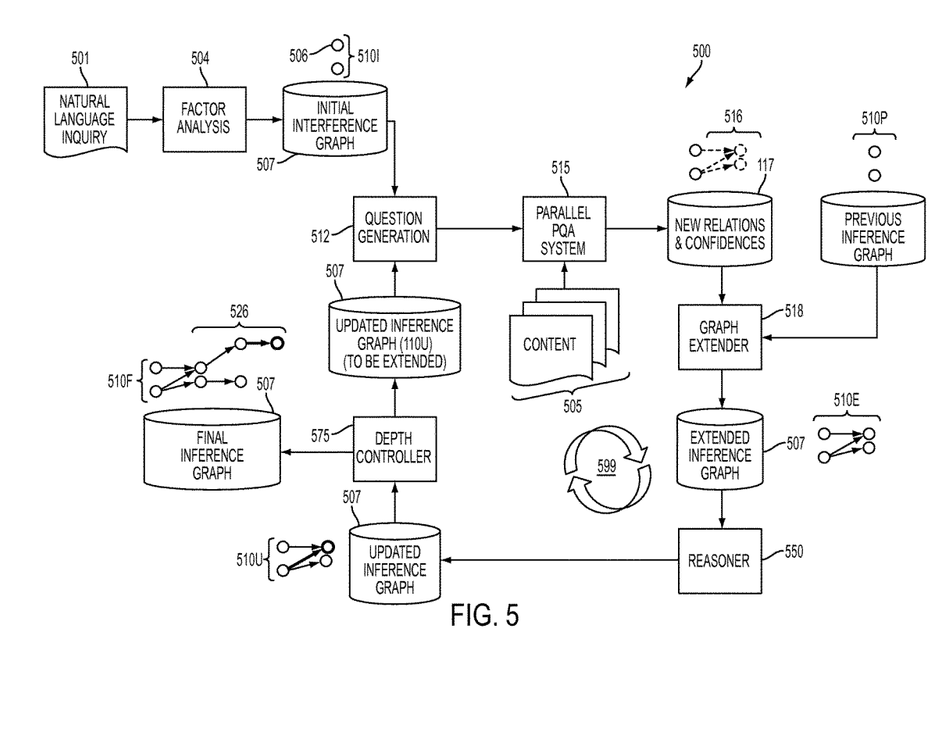
FIG. 5 depicts a high-level block diagram of a schematic of a text-based inference engine where embodiments of influence filtering can be implemented in accordance with an embodiment.

Turning now to FIG. 5, a high schematic of a text-based inference engine 500 where embodiments described herein can be utilized is generally shown. The text-based inference engine 500 can be implemented by a computer system employing one or more computing devices that perform an iterative process 599 that generates a final inference graph 510F given an input inquiry 501, a set(s) of factors, and determined relations. The text-based inference chaining engine 500 shown in FIG. 5 first implements a factor analysis component 504 implementing programmed processes to extract factors 506 from the input inquiry 501. Programmed processes further generate an initial inference graph 510I using factors extracted from the inquiry. This initial inference graph 510I may only include factors 506 extracted from the inquiry as initial end-points or nodes. This initial inference graph 510I may be stored as data in a storage device 507. Iterative processes 599 can further discover relations to a new set of concepts from the factors 506 that may lead to answers or solutions.

In one aspect, the text-based inference engine 500 provides a system and method that discovers and justifies answers to inquiries by constructing inference graphs over content connecting factors to answers such that each relation in an inference graph is justified by one or more passages from the content and where the inference graph may connect factors to answers over a path containing one or more edges (i.e., multi-step inference graph). Unstructured content is textual data (e.g., books, journals, web pages, documents etc) and is typically used as a source for answers and as a source for justifications of those answers. Is further used to justify or evidence the answer to a question or more specifically the truth of a relation (note: it can consider non-text to determine this). More generally, unstructured content may refer to a combination of text, speech and images. Structured content is any database or knowledgebase where data is encoded as structured relations. A relational database is typical as is a logical-based knowledgebase. Content is any combination of unstructured and structured content.

At the start of the iteration(s), from the generated initial inference graph 510I (or a generated updated inference graph 510U to be extended in a subsequent iteration), a question generator 512 implements a programmed process to first generate questions for the probabilistic question answer (PQA) system 515 to answer. A PQA system 515 is any system or method that produces answers to questions and may associate those answers with confidences indicating the likelihood the answers are correct, and that may associate answers with a passage-based justification that are intended to explain to humans why the answer is likely correct. A question is a single sentence or phrase in natural language (e.g., English) or a formal language (e.g., first order logic) that intends to ask for the end point(s) of a relation or to ask whether or not a relation between two concepts is true. One example is: "What does aspirin treat?"/ treat(aspirin, X). Another example of a question is: "Does Aspirin treat Strokes?"/treat(aspirin, strokes).

An answer or solution is an element of text—a word, number, phrase, sentence, passage or document. An answer is thought to be correct or partially correct with respect to a question or inquiry if a human considers it useful response to the question or inquiry. In the case of a simple question or relation, the answer is typically the sought-after end-point of the relation, e.g., "Who discovered America in 1492?" The answer is the missing concept, X in the relation "X discovered America".

As revised inference graphs are generated at each iteration new questions may be generated for PQA system 515 to answer. Particularly, at each iteration for every new end-point of every new relation in the inference graph, the question generator 512 formulates one or more questions for the PQA system 515 to answer. Parallel implemented PQA system 515 receives the formulated questions based on the prior inference graph, e.g., graph 510P. Based on the number of independent questions generated, one or more PQA systems 515 may be called in parallel to discover new relations that answer the questions. The PQA system 515 is a type of natural language question-answering system that takes in a natural language question and returns a set of possible answers, a confidence score for each answer indicating a probability the answer is correct, and a set of justifying passages for each answer extracted from the body of content that provides evidence for why the answer may be correct. In one embodiment, IBM DeepQA system may be implemented as the PQA system 515. Other possible QA systems that may be implemented as possible embodiments for the PQA system are Javellin (CMU), Ephera(CMU and Open-Source), SMART(MIT), Wolfram Alpha(Wolfram). These each attempt to produce precise answers to natural language questions but vary in their ability to produce confidence scores and justifying passages.

The PQA system 515 performs processes to obtain or discover new relations 516 that answer the questions from the structured or unstructured content 505. The discovered new relations 516 additionally include confidences and may be stored as data in a storage device 517 which may be or include the storage device 507.

As further shown in FIG. 5, in a current iteration, a graph extender component 518 implements programmed processes to receive the stored new relations and confidences data 517 and extends the previous inference graph 510P generated in the immediately prior iteration (e.g., which is 510I at the first iteration) based on the new relations and confidences data 517. Particularly, graph extender 518 receives the new relations and confidences 517 and processes the new relations by merging them into the previous inference graph 510P to result in a new extended inference graph 510E shown as output from the graph extender 518 and may be stored as data in a storage device 507.

More particularly, the graph extender 518 takes as input the previous inference graph 510P and a set of new relations 516 discovered by the PQA component and outputs a new inference graph 510E that includes the new relations. It performs this by merging nodes in the input inference graphs with nodes in the new relations and adding them to the graph. An example follows:
    Input: Inference Graph: A→B→C
    Input: New Relations: C1→D
    Output: A→B→(C/C1)→D
where C and C1 where merged (considered the same node). The computed confidence on C/C1→D is the same confidence produced by the PQA 515 system's answer to the question about C that produced C1→D.

In one embodiment, merging nodes may be implemented using some form of "specialization". For example, if C was "diabetes", and D was "blindness", the question generated was "What causes blindness?" and the PQA system produces and relation "diabetes mellitus causes blindness" then the graph extender 518 would merge "diabetes" with "diabetes mellitus". In this case the embodiment may only merge nodes if they were identical or if answer was a connected to a more specific concept. Thus, "diabetes" would merge with "diabetes" or with "diabetes mellitus". At this point, confidences are not re-propagated over the extended graph 510E as this is performed by the reasoner component 550.

As shown in FIG. 5, the reasoner component 550 performs programmed processes to propagate computed confidences across the relations to output an updated (for the current iteration) inference graph 510U assured of a particular confidence level across the relations. That is, as part of the reasoner process, additional pruning may be performed as certain relation confidences generated by the PQA system may drop below a set threshold. It may also merge relations based on similarity metrics.

In one embodiment, the reasoner component 550 receives as input: (1) a set of relations between inference graph nodes, (2) factors, and (3) candidate solutions or answers; and outputs a probability for each node in the inference graph. The reasoner component 550 may also optionally output an explanation of why the answer was correct.

Returning to FIG. 5, a depth controller component 575 performs processes to receive the new updated inference graph 510U, and determines a need to halt the iteration based on the specified depth or other criteria. The depth controller component 575 provides the ability for the inference chaining system and method to iteratively extend the initial inference graph formed from the original factors output by factor Analysis. This iterative process will continue to grow the graph unless it is stopped and the depth controller component 575 provides the ability to halt the iterative process based on a specified depth or other criteria.

At each iteration the depth controller component 575 performs a method to analyze the current updated inference graph 510U, and decides if the graph should be considered final and the process halted. The depth controller may be implemented in a variety of ways. For example, the depth controller may look for a pre-determined depth represented by an integer considered the "Depth Threshold" (DT) value, for example, determining if the current iteration has a DT value of 2. In this example, once a graph has extended two steps (relations) from the original factors the iteration will stop and the graph is output as final. Another embodiment may consider a "Confidence Threshold" (CT) value, for example, determining there is a node in graph 510U that has confidence>=CT. In this example, the depth controller 575 would halt the iteration and output the graph 510U as a final inference graph 510F if it contained any node that was associated with a confidence higher than a given CT value. Any combination of depth and confidence threshold may be used in an embodiment of the depth Controller 575. For example the system may halt and output the final graph if the depth controller detects if the graph has reached a certain depth or if it contains a high-confidence node—whichever comes first.

Referring back to FIG. 5, if a need to halt the iteration is determined, the updated inference graph 510U is output as the final inference graph 510F and stored in a storage device 507. At that point final inference graph 510F will include a set of nodes and relations 526 that satisfy the depth or confidence criterion. Otherwise, the updated inference graph 510U is to be extended and is provided as input to question generator component 512 as a new inference graph of nodes and relations for the next iteration 599.

Embodiments of the present invention can be used as part of the reasoner component 550 shown in FIG. 5. The graphs given to the reasoner component 550 can be graphs constructed from knowledge. One way of performing the functions of the reasoner component 550 is through probabilistic inference over graphical models. Embodiments described herein apply to both.

Figure 6:
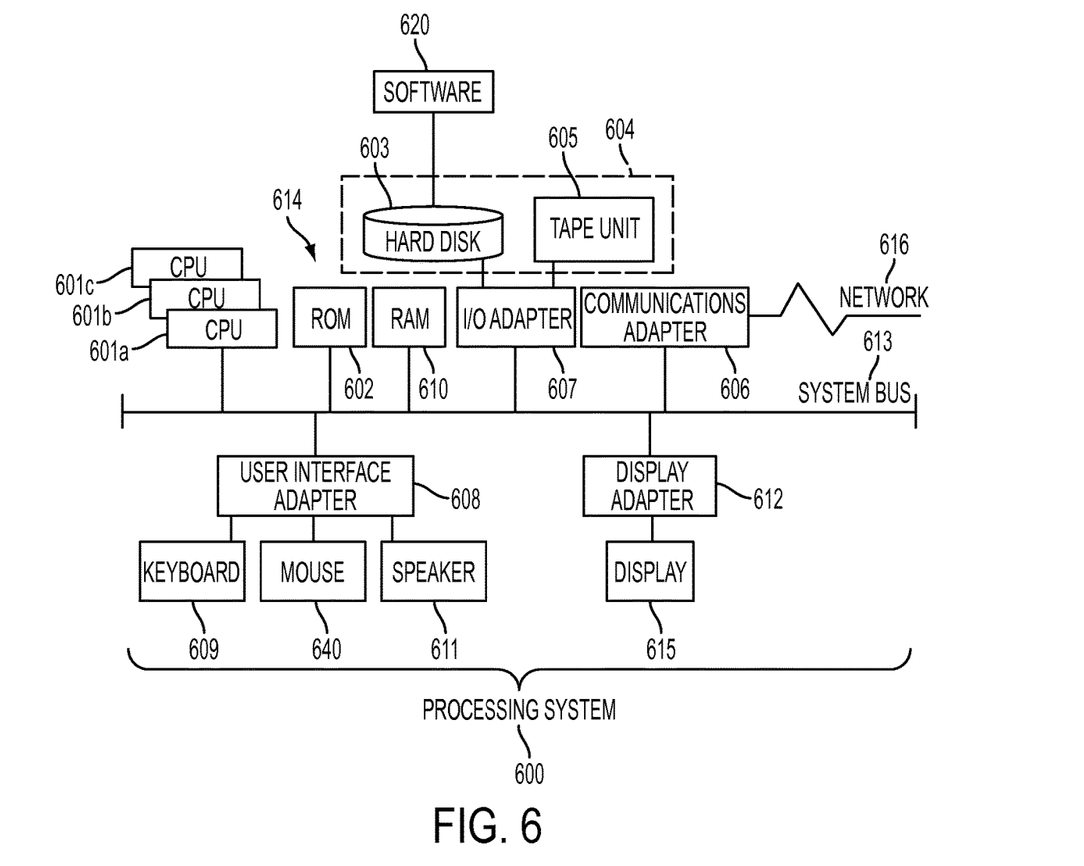
FIG. 6 depicts a processing system in accordance with an embodiment.

Referring now to FIG. 6, there is shown an embodiment of a processing system 600 for implementing the teachings herein. In this embodiment, the processing system 600 has one or more central processing units (processors) 601a, 601b, 601c, etc. (collectively or generically referred to as processor(s) 601). Processors 601, also referred to as processing circuits, are coupled to system memory 614 and various other components via a system bus 613. Read only memory (ROM) 602 is coupled to system bus 613 and may include a basic input/output system (BIOS), which controls certain basic functions of the processing system 600. The system memory 614 can include ROM 602 and random access memory (RAM) 610, which is read-write memory coupled to system bus 613 for use by processors 601.

FIG. 6 further depicts an input/output (I/O) adapter 607 and a network adapter 606 coupled to the system bus 613. I/O adapter 607 may be a small computer system interface (SCSI) adapter that communicates with a hard disk 603 and/or tape storage drive 605 or any other similar component. I/O adapter 607, hard disk 603, and tape storage drive 605 are collectively referred to herein as mass storage 604. Software 620 for execution on processing system 600 may be stored in mass storage 604. The mass storage 604 is an example of a tangible storage medium readable by the processors 601, where the software 620 is stored as instructions for execution by the processors 601 to perform a method, such as the process flow of FIG. 3. Network adapter 606 interconnects system bus 613 with an outside network 616 enabling processing system 600 to communicate with other such systems. A screen (e.g., a display monitor) 615 is connected to system bus 613 by display adapter 612, which may include a graphics controller to improve the performance of graphics intensive applications and a video controller. In one embodiment, adapters 607, 606, and 612 may be connected to one or more I/O buses that are connected to system bus 613 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 613 via user interface adapter 608 and display adapter 612. A keyboard 609, mouse 640, and speaker 611 can be interconnected to system bus 613 via user interface adapter 608, which may include, for example, a Super I/O chip integrating multiple device adapters into a single integrated circuit.

Thus, as configured in FIG. 6, processing system 600 includes processing capability in the form of processors 601, and, storage capability including system memory 614 and mass storage 604, input means such as keyboard 609 and mouse 640, and output capability including speaker 611 and display 615. In one embodiment, a portion of system memory 614 and mass storage 604 collectively store an operating system such as the AIX® operating system from IBM Corporation to coordinate the functions of the various components shown in FIG. 6.

Technical effects and benefits include the ability to build a graphical model from relations that include dependent relations. A strength of a relation between two items can be correctly reflected in a graphical model by taking into account the influence of additional paths between the two items in the graphical model.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer program product comprising:
   a tangible storage medium readable by a processing circuit and storing instructions for execution by the processing circuit to perform a method comprising:
   accessing a graphical model in a data store, the graphical model comprising a plurality of nodes, the nodes connected by edges having edge strengths representing a degree of relation between the nodes;
   receiving a target relation strength for a pair of nodes in the graphical model;
   determining an edge strength of an edge in a direct path between the pair of nodes, the determining comprising:
      traversing, in the graphical model, one or more paths other than the direct path between the pair of nodes;
      estimating a cumulative strength of the traversed paths; and
      calculating the edge strength for the edge in the direct path based on the cumulative strength of the traversed paths and the target relation strength, the calculating comprising:
         subtracting the cumulative strength from the target relation strength; and
         setting the edge strength of the edge in the direct path to the result of the subtracting based on the result being a positive number; and
   assigning the calculated edge strength to the edge in the direct path between the two nodes.

2. The computer program product of claim 1, wherein the graphical model was generated using a knowledge based method.

3. The computer program product of claim 1, wherein the receiving, determining, and assigning are performed for a plurality of pairs of nodes.

4. The computer program product of claim 1, wherein the calculating further comprises setting the edge strength of the edge in the direct path to zero based on the result being less than or equal to zero.

5. The computer program product of claim 1, wherein the traversing paths includes traversing only the paths between the two nodes having a length that is less than a specified length.

6. The computer program product of claim 1, wherein the traversing is performed recursively.

7. A system comprising:
a memory having computer readable instructions; and
a processor for executing the computer readable instructions, the computer readable instructions including:
accessing a graphical model in a data store, the graphical model comprising a plurality of nodes, the nodes connected by edges having edge strengths representing a degree of relation between the nodes;
receiving a target relation strength for a pair of nodes in the graphical model;
determining an edge strength of an edge in a direct path between the pair of nodes, the determining comprising:
traversing, in the graphical model, one or more paths other than the direct path between the pair of nodes;
estimating a cumulative strength of the traversed paths; and
calculating the edge strength for the edge in the direct path based on the cumulative strength of the traversed paths and the target relation strength, the calculating comprising:
subtracting the cumulative strength from the target relation strength; and
setting the edge strength of the edge in the direct path to the result of the subtracting based on the result being a positive number; and
assigning the calculated edge strength to the edge in the direct path between the two nodes.

8. The system of claim 7, wherein the graphical model was generated using a knowledge based method.

9. The system of claim 7, wherein the traversing is performed recursively.

* * * * *